United States Patent [19]
Colman et al.

[11] Patent Number: 5,657,750
[45] Date of Patent: Aug. 19, 1997

[54] FLUID FILTERING DEVICE UTILIZABLE WITH GAS MONITORS

[75] Inventors: Lewis Colman; Gershon Levitzky, both of Jerusalem, Israel

[73] Assignee: IRAD Technologies Ltd., Jerusalem, Israel

[21] Appl. No.: 535,345

[22] Filed: Sep. 29, 1995

[30] Foreign Application Priority Data

Oct. 4, 1994 [IL] Israel ................................. 111162

[51] Int. Cl.⁶ .......................................... A61B 5/00
[52] U.S. Cl. .................. 128/205.12; 128/204.13; 128/205.27; 128/205.29; 604/406
[58] Field of Search ........................ 128/200.24, 205.12, 128/204.13, 204.14, 204.15, 204.16, 204.17, 205.27, 205.29, 205.23, 719; 96/6, 11; 95/46, 54; 55/270; 604/406

[56] References Cited

U.S. PATENT DOCUMENTS

| | | | |
|---|---|---|---|
| D. 309,349 | 7/1990 | Martikainen et al. | 128/204.22 |
| 3,422,008 | 1/1969 | McLain | 210/646 |
| 3,803,810 | 4/1974 | Rosenberg | 128/205.12 |
| 4,267,053 | 5/1981 | Hashino et al. | 210/650 |
| 4,268,279 | 5/1981 | Shindo et al. | 95/46 |
| 4,327,718 | 5/1982 | Cronenberg | 128/205.12 |
| 4,456,014 | 6/1984 | Buck et al. | 128/204.22 |
| 4,558,708 | 12/1985 | Labuda et al. | 128/207.14 |
| 4,568,366 | 2/1986 | Frederick et al. | 55/159 |
| 4,579,568 | 4/1986 | Ricciardelli et al. | 128/205.12 |
| 4,612,019 | 9/1986 | Langhorst | 95/52 |
| 4,615,694 | 10/1986 | Raines | 604/406 |
| 4,666,649 | 5/1987 | Krueger et al. | 95/54 |
| 4,668,401 | 5/1987 | Okumura et al. | 210/650 |
| 4,678,488 | 7/1987 | Howard et al. | 55/406 |
| 4,679,573 | 7/1987 | Parnoff et al. | 128/205.12 |
| 4,713,095 | 12/1987 | Ricciardelli | 55/189 |
| 4,824,444 | 4/1989 | Nomura | 95/54 |
| 4,844,719 | 7/1989 | Toyomoto et al. | 55/16 |
| 4,852,583 | 8/1989 | Walker | 128/208.26 |
| 4,886,528 | 12/1989 | Aaltonen et al. | 128/204.18 |
| 4,924,860 | 5/1990 | Larsen et al. | 128/205.12 |
| 4,929,259 | 5/1990 | Caskey et al. | 55/158 |
| 4,985,055 | 1/1991 | Thorne et al. | 128/205.12 |
| 5,002,590 | 3/1991 | Friesen et al. | 55/158 |
| 5,026,479 | 6/1991 | Bikson et al. | 210/321.8 |
| 5,035,236 | 7/1991 | Kanegaonkar | 128/205.27 |
| 5,049,170 | 9/1991 | Parnoff | 55/323 |
| 5,064,418 | 11/1991 | Cronin | 604/190 |
| 5,067,971 | 11/1991 | Bikson et al. | 55/16 |
| 5,071,552 | 12/1991 | Bikson et al. | 210/321.8 |
| 5,101,817 | 4/1992 | Etter | 128/208.26 |
| 5,131,387 | 7/1992 | French | 128/205.27 |
| 5,158,581 | 10/1992 | Coplan | 55/16 |
| 5,160,042 | 11/1992 | Bikson et al. | 210/321.8 |
| 5,160,511 | 11/1992 | Lovelock | 55/16 |
| 5,221,474 | 6/1993 | Yokono et al. | 604/406 |
| 5,282,964 | 2/1994 | Young et al. | 210/321.8 |
| 5,293,875 | 3/1994 | Stone | 128/205.23 |
| 5,365,938 | 11/1994 | Eskula | 128/719 |
| 5,380,433 | 1/1995 | Etienne et al. | 210/321.79 |
| 5,398,677 | 3/1995 | Smith | 128/205.12 |

FOREIGN PATENT DOCUMENTS

| | | |
|---|---|---|
| A-275105 | 7/1988 | European Pat. Off. . |
| A-549266 | 6/1993 | European Pat. Off. . |
| 2229650 | 3/1990 | United Kingdom . |
| WOA9101771 | 2/1991 | WIPO . |

*Primary Examiner*—Vincent Millin
*Assistant Examiner*—V. Srivastava
*Attorney, Agent, or Firm*—Frishauf, Holtz, Goodman, Langer & Chick, P.C.

[57] ABSTRACT

A fluid filtering device for separating liquid from gases to be analyzed, including a tubular housing defining a space therein and having inlet and outlet end portions delimiting passageways in fluid communication with the space, the portions being connectable between a source of fluid and a gas analyzer, and a liquid/gas hydrophobic hollow fiber filter element located within the tubular housing preventing material other than gases to pass therethrough. The tubular housing and filter element form a small volume within the housing, and the device is effectively operable independent of its orientation, or field of gravitation acting thereon.

33 Claims, 5 Drawing Sheets

FLUID FILTERING DEVICE UTILIZABLE WITH GAS MONITORS

BACKGROUND OF THE INVENTION

The present invention relates to a fluid filtering device and particularly to a filter for separating liquid from gases. More specifically, the present invention is concerned with a filtering device utilizable with a gas analyzer or monitor, having a very limited effect on the response time of the monitor to changes of the gas content and being independent of the orientation of the device or of the field of gravitation acting thereupon.

The current state of the art of filters for gas analyzers can be divided into two categories:—technologies based on hydrophobic microporous membranes, and mechanical separators.

Gas filters based on the first technology commonly use flat sheets of hydrophobic microporous membranes embodied within an appropriate housing, whose structure is designed to both collect the trapped liquid and for connection with the analyzers or monitors.

In many applications (specifically capnographs—$CO_2$ respiration monitors), it is required that the gas flows through the filtering media without the wave form of the gas being disturbed. This is required so that the measured changes in time of the gas constitution originate only from the breath under test and not those introduced later by parts of the flow system, which transfers the gas to the measuring region. A measure of merit for a filtering device reflecting its ability to freely transfer gases is defined by the response time it invokes. In general, the response time is a measure of response to a change in gas constituent. A long response time will distort the output display even at low breathing rates and such distortion may affect the accuracy of the tested information regarding a patient's health condition displayed on, or recorded by, the analyzer or monitor.

When working with low gas flow rates, as is typical with capnographs, in order to create a gas filter with minimum distortion to the gas wave form providing short response times, the filter should provide minimal turbulence and resistance to a laminar flow and have no fluid passageways through which the gas passes, which due to shape, size or material thereof, disturb the wave form. For example, the shape and size of the fluid passageways must be such that no abrupt changes in dimensions or volume thereof when entering the filter be permitted. Otherwise, the gas entering enlargements in the passageways will possess very different flow rates along the radius perpendicular to the direction of gas flow upstream therefrom. Regions furthest away from the center of the passageways may have very slow flow rates relative to the center. Such a distribution of fluid flow rates will mix gases coming at different times from the patient and hence impair the response time. To an extent, this disturbance of smooth flow is dependent on the size and abruptness of the enlargement. When using flat sheet membranes for filtering purposes, in order to provide as large a surface area of the membrane material as required, a large volume with abrupt changes in dimensions is inevitable.

Further, if the gas must pass either between or through porous walls (used to either soak up liquid or as a filter media) which have a substantial thickness (e.g. more than 0.5 mm), then the free and unimpaired flow of gas will be disturbed by parts of the gases diffusing within and outside of the porous walls, where the flow is hindered relative to the flow of the gases not entering the porous material, thereby causing a mixing of the gas.

Hence, distortion to smooth unimpaired gas flow in the prior art fluid filters are caused by three major factors:

a) by the materials of the filtering device itself, including the porous material of the filtering membrane and porous portions of the walls thereof, to an extent proportional to their thickness;

b) by the shape or configuration of the filter body itself, presenting abrupt changes in the gas passageway between inlet and outlet thereof, and c) by the overall size of the volume or space of the passageway for the gas flow from the inlet to the outlet of the filter.

These three factors relating to the passageway where the fluid to be filtered inside the filter traverses, is also referred to herein as "space". It has been found that in order to achieve effective analysis of the characterisitics of the filtered fluid, the filter should have as little "dead space" as possible, namely, the space in which the above three factors prevail and which factors are detrimental to the optimal analysis, should be minimal.

In attempting to overcome the disadvantages of the above-described fluid filters, in certain instances there has been applied means for continuously removing the trapped liquid away from the membrane surface to be collected/discarded by a separate feature of the monitor. This more complicated solution, which permits the use of a smaller sized membrane, still requires a minimum sized flat membrane in order not to produce too high a resistance to flow with its inevitable drawbacks of undesired sizes and shapes and obligates a defined orientation for its correct operation. This pre-defined orientation, which is also a fundamental requirement in mechanical filters, is not always possible for implementation since, in many applications, for example, transportable monitors, the filter must operate while the monitor is oriented in any direction.

The filtering device of the present invention is especially advantageous for filtering small or minute volumes of fluid, for example, fluids extracted for analysis from neonatals and the aged.

It is therefore a broad object of the present invention to provide a fluid filtering device to be used in conjunction with a gas monitor or analyzer having a construction having a limited interference to the gas flow.

It is a further broad object of the present invention to provide a fluid filtering device to be used in conjunction with a gas monitor or analyzer, whose orientation will not impede the proper operation of the filtering device, and which is independent of the field of gravity acting thereupon.

It is a still further object of the present invention to provide a fluid filtering device having means for trapping and collecting filtered out non-gaseous components, without the trapped and collected components impairing the gas flow.

SUMMARY OF THE INVENTION

In accordance with the present invention there is therefore provided a fluid filtering device for separating liquid from gases to be analyzed, comprising a tubular housing defining a space therein and having inlet and outlet end portions delimiting passageways in fluid communication with said space, said portions being configured to be connectable between a source of fluid and a gas analyzer, and a liquid/gas hydrophobic hollow fiber filter element located within said tubular housing preventing material other than gases to pass therethrough, said tubular housing and filter element forming a small volume within said housing, and said device being effectively operable independent of its orientation, or field of gravitation acting thereon.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE INVENTION

Figure 1:
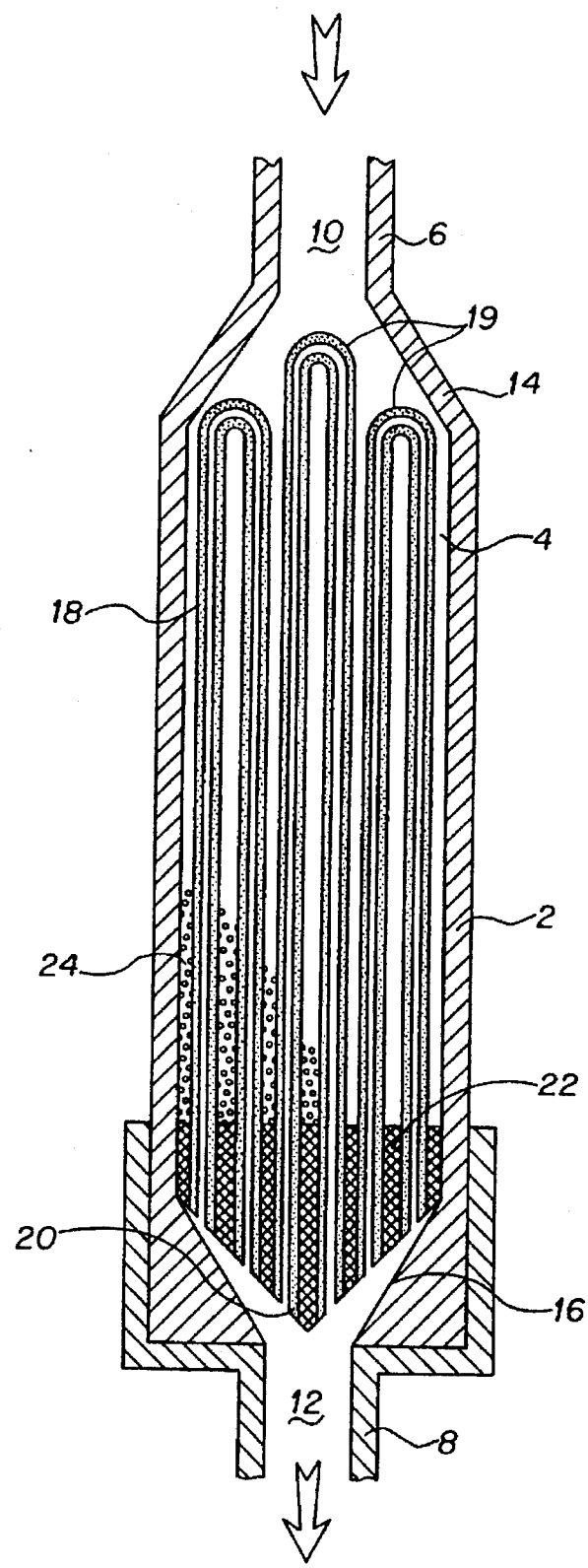
FIG. 1 is a view in cross-section of the filtering device according to a first embodiment of the invention, wherein the filtered liquid is collected in the tubular housing.

There is shown in FIG. 1 a cross-sectional view of the fluid filtering device for separating liquid and solid particles from gases to be analyzed or monitored, which device includes a tubular housing 2 of a relatively small diameter, defining a space 4 therein and having an inlet end portion 6 and an outlet end portion 8 defining therein fluid flow passages 10 and 12, respectively. The end portions 6 and 8 are utilizable for connecting the device between a source of fluid and a gas analyzer or monitor and may be provided with any connector appropriate for this purpose. As seen, the inlet and outlet end portions 6 and 8 are configured to provide smooth and gradual transition sections 14 and 16 between the relatively larger internal space 4 of the housing 2 and the internal passageways 10 and 12 of the end portions 6 and 8, respectively.

Inside the housing 2 is disposed a fluid filter element 18, composed of a hydrophobic hollow fiber filter. The filter element 18 is preferably formed by folding over the fibers, thus providing a first closed end portion 19 and a second open end portion 20. The filter element 18 is shaped and located inside the housing 2 such that the first closed end portion 19 reaches the space delimited by the transition section 14 and the second open end portion 20 reaches the space delimited by the transition section 16. Advantageously the internal diameters of the housing 2 and the end sections 6 and 8 are calculated so that the cross-sectional area of the free space inside the housing, i.e., the space unoccupied by the filter element 18 and the passageways 10 or 12 are substantially the same. The hollow fibers of filter element 18, in conjunction with the small diameter tubular housing 2, form a filtering device having at least four times smaller volume per square centimeter of filter material or of effective filter area than the dead space obtained utilizing a filter element of the flat membrane type. In order to assure that non-filtered fluid will not reach the outlet end portion 8, blocking material 22 is inserted in between the hollow fibers and the inner surface of the wall of the housing 2 at the second end portion 20. The filtering device may include means 24 for further reducing the dead space within the housing 2. Such means may be embodied by non-permeable material, e.g., glass particles or beads, as illustrated in FIG. 1.

The closed end portion 19 of the filter element 18, as well as the walls along the entire fibers, provide thin walls through which the gas of the fluid to be filtered traverses with minimal disturbance. Hence, in the overall effort to provide an efficient fluid filter through which fluid can pass from the inlet to the outlet with minimal pressure applied thereto and with minimal disturbance, there is provided a combination of elements cooperating in achieving same. The elements include:

a) the first transition section 14 preventing an abrupt transition of fluid flow from the inlet portion 10 to the space 4 inside the housing, partially occupied by the filter;

b) a filter composed of hollow fibers closed at one end and open at the other, so as to cause the incoming fluid to pass only a thin wall prior to reaching the passageways inside the fibers, which passageways smoothly guide the filtered fluid from the inlet portion to the outlet portion, and c) the filtered fluid exiting the filter reaches a second transition section 16 before arriving at the outlet end portion 12.

In order to improve smooth and undisturbed fluid flow even further, the outlet portion of the filter through which filtered fluid gradually exits the fibers, i.e., the fibers at the outlet portion, is shaped so that the edges of the fibers do not terminate at one plane, but rather terminate at different cross-sectional planes, thereby causing the filtered fluid to exit the fibers across several planes when leaving the passageways and entering the transition section. Thus, during the entire filtering process, the fluid to be filtered is very carefully treated to avoid the mixing of the gas constituents while being flown into the monitor and similar disturbances in flow, which mixing of gases greatly increases the response time of the system to which the filtering device is connected. In other words, the structure of the filter, according to the present invention, effects the filtering of the fluid while preserving as much as possible the continuity of the patient's breath, as exhaled.

It has been found that for a monitor sampling at flow rates lower than 50 ml/min, the average diameter of the tubular housing 2 should be less than 2.5 mm, if no means 24 are included. For higher flow rates, however, the average diameter of the tubular housing 2 can be increased accordingly, for example, for flow rates of approximately 150 ml/min, a diameter of up to 3.5 mm could be used.

The liquid collected during use of the device will gradually immerse portions of the filter element 18, rendering those parts inactive. Eventually, when at least the major portion of the filter element is submerged, the filtering device becomes ineffective, and is replaced.

Figure 2:
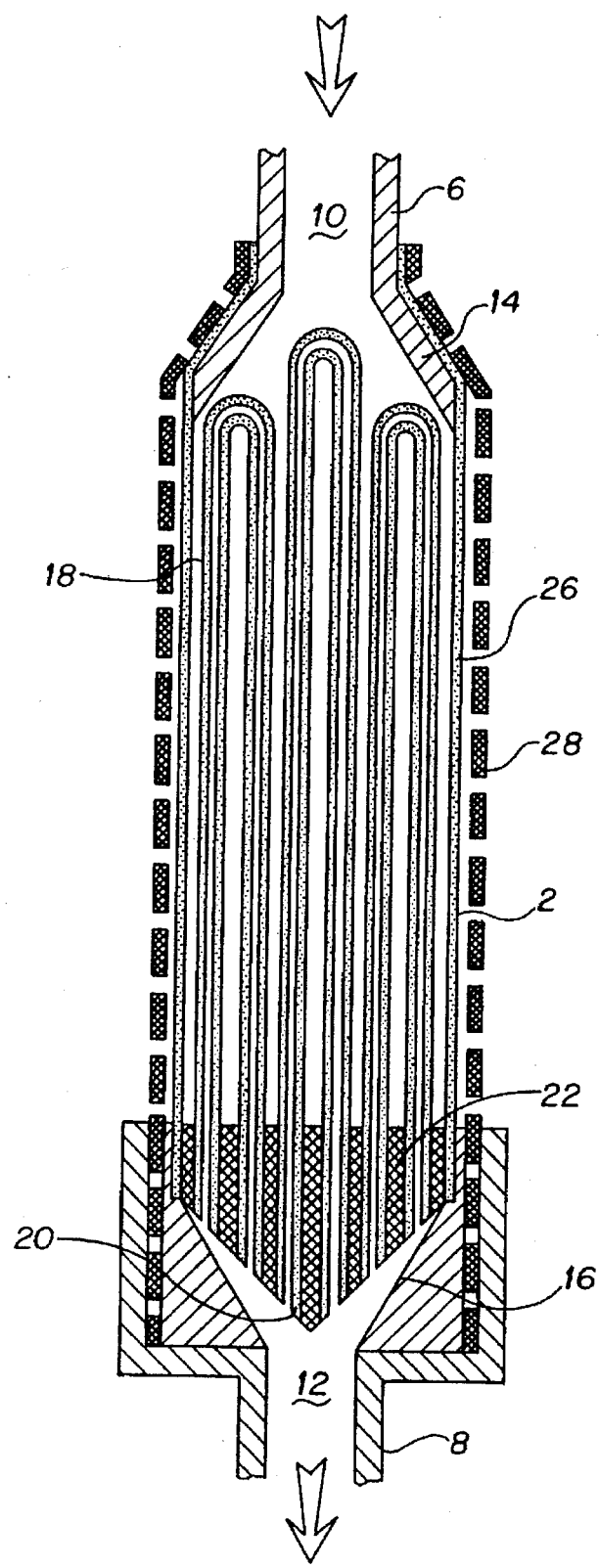
FIG. 2 is a view in cross-section of the filtering device according to a second embodiment of the invention.

In order to prolong the effective usable life time of the filter device according to a further embodiment of the present invention illustrated in FIG. 2, the tubular housing 26, or a portion thereof, is made of suitable liquid permeable material allowing the traversing of humidity, moisture and liquids, but preventing the traversing of gases. An example of such material is Nafion. Hence, the filtered out liquid, or at least some of it, is continuously removed from the device through the wall of the housing 26. In order to protect the Nafion-made housing wall against bending, which is detrimental to smooth fluid flow, the wall is covered with a braided sleeve 28, for example, a plastic sleeve. Such a sleeve allows continuous ventilation of the Nafion wall, while guarding same against bending and damage.

Figure 3:
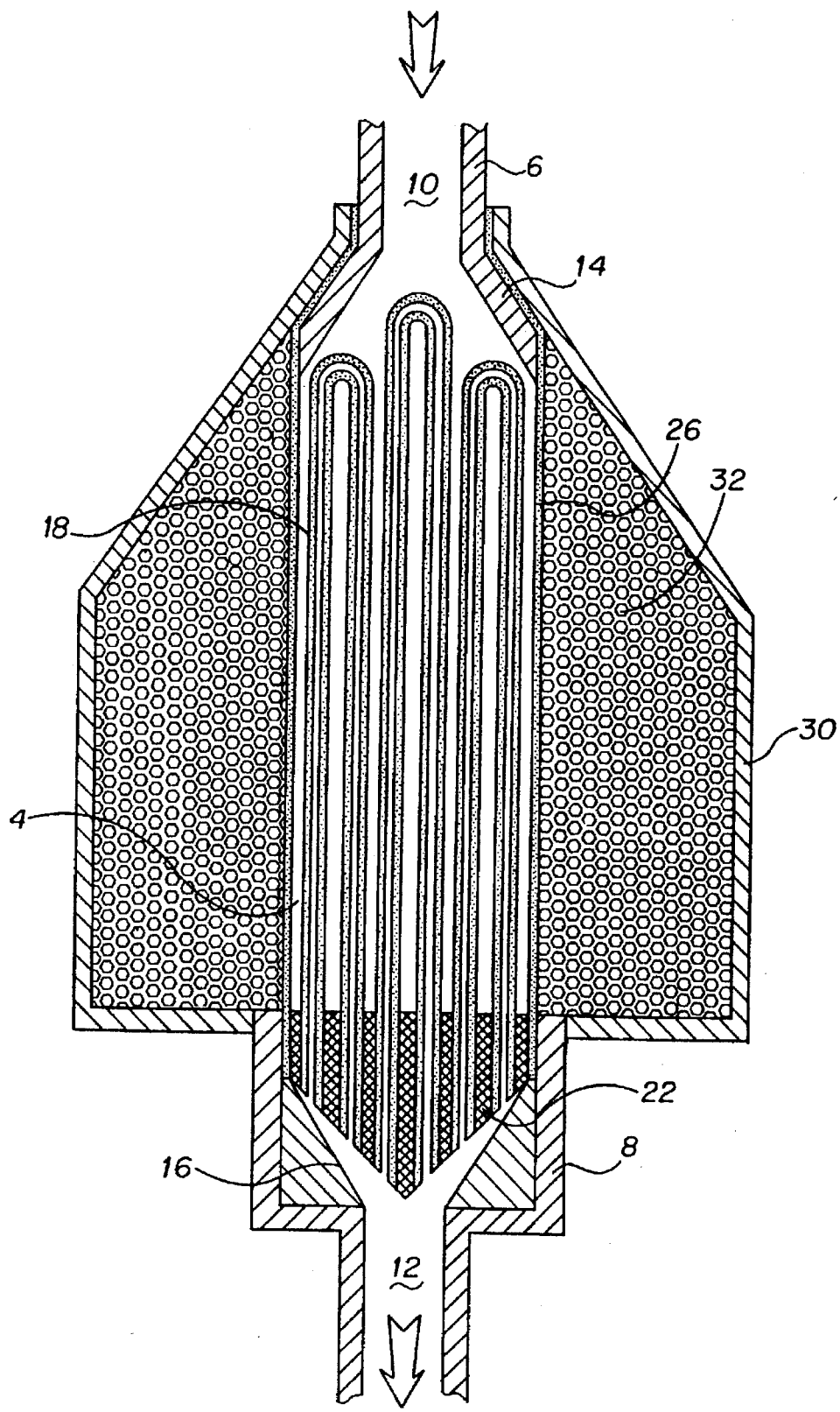
FIG. 3 is a cross-sectional view of the filtering device of FIG. 2 providing a further compartment for collecting the filtered liquid.

Referring to FIG. 3, there is shown an embodiment of the filtering device of the type furnished with a housing 26 made of a material allowing the traversing of humidity and moisture, as described above. The housing 26 is enclosed by a jacket 30 defining thereinbetween a liquid retaining space. Advantageously the jacket 30 encapsulates liquid absorbing material 32, such as silica gel. This material 32 is used to absorb the fluid transferred through the wall of the housing 26 from within the space 4 to the outside. In this manner, the wall is kept dry, thereby enhancing the liquid transfer capabilities of the housing wall.

Figure 4:
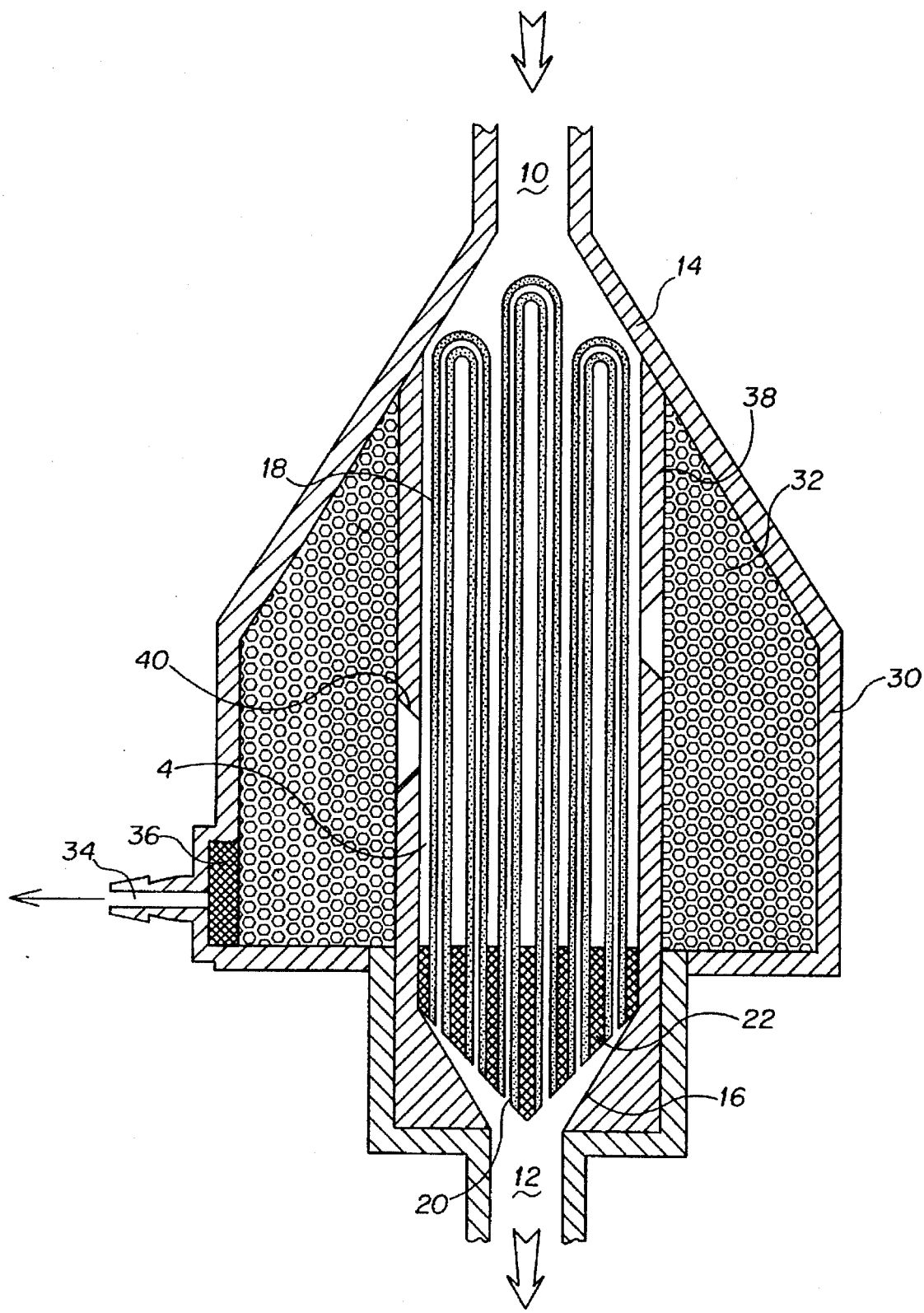
FIG. 4 is a cross-sectional view of another embodiment of the filtering device according to the invention, providing bypass means for removing and collecting filtered liquid in a further compartment.

In cases where a substantial amount of filtered out liquid is to be removed, further means for more positive removal of filtered out liquid can be provided, as illustrated in FIG. 4. Such means include a nozzle 34 connectable to a vacuum pump applying a suction action to the interior of the envelope 30. At the entrance to the nozzle 34, there may be introduced a hydrophobic filter 36 preventing liquid from reaching the pump. In the wall of housing 38 there are formed openings 40, through which openings accumulated liquid can pass.

Figure 5:
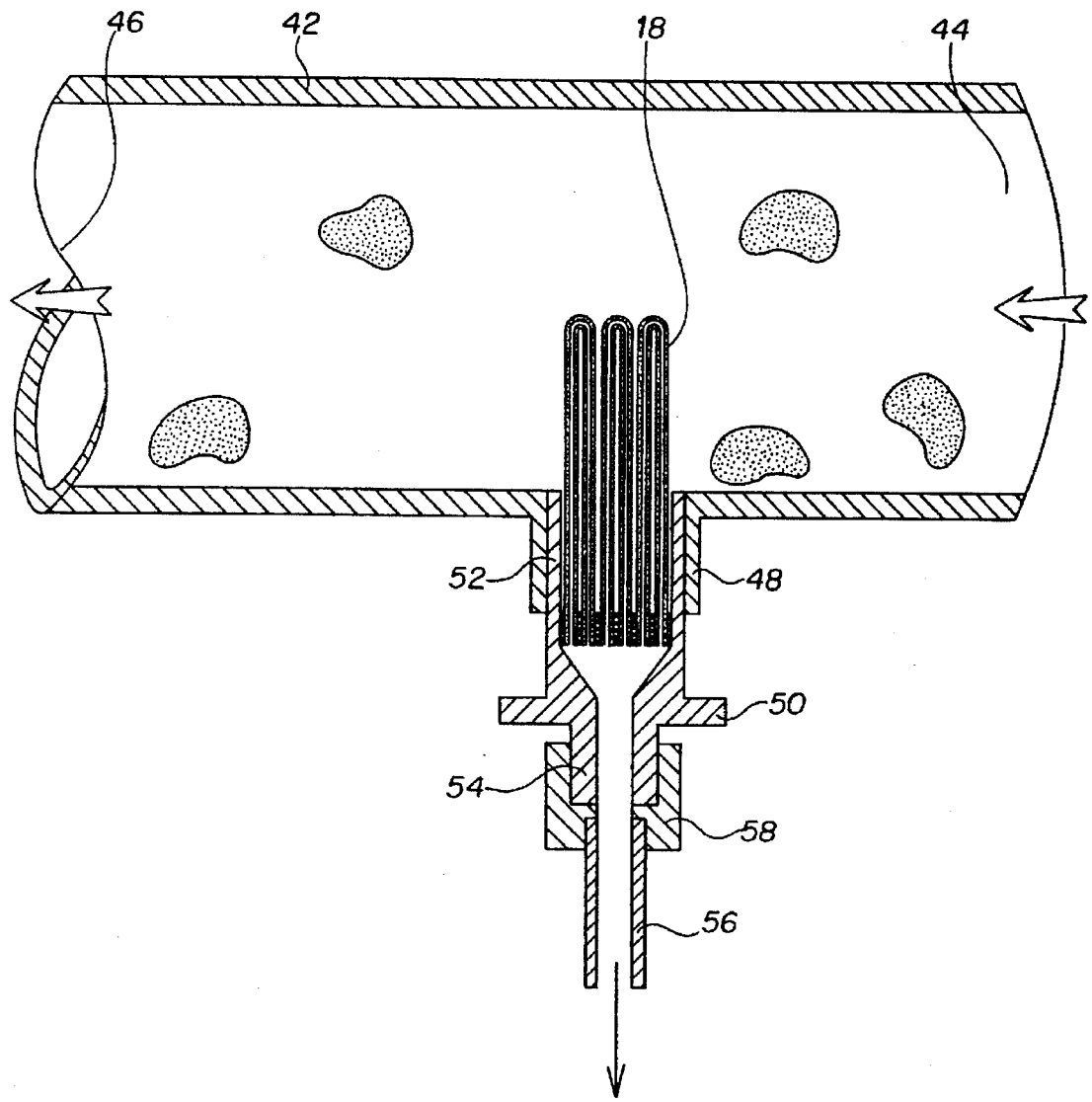
FIG. 5 is a view in partial cross-section of still a further embodiment of the invention.

The embodiment illustrated in FIG. 5 is adapted to be utilized with a patient's ventilation system, incorporating a T-piece 42. One opening 44 of the T-piece 42 leads to a patient's mouth, while the opposite opening 46 leads to a ventilation system. To the third opening 48 there is coupled a hollow fiber filter element 18. The element 18 is mounted in a unit 50, having a first portion 52, configured to be inserted and retained in the opening 48 of the T-piece 42, and a nozzle portion 54, Which is in fluid communication through the filter 18 with the T-piece 42. A tube 56 having a standard connecting socket 58 at one end and leading to a gas analyzer or monitor can be easily attached to the nozzle portion 54. The entire unit 50 is thus disengageable and replaceable.

As further seen in the figure, since the airway of the T-piece 42 is rather large, there is obtained a relatively large filtering area. The sample tube 56 sucks only clean gas, hence a gas analyzer or monitor connected thereto has to deal only with condensed humidity gas, whereas human excretions (saliva, blood or other liquids), are prevented from entering the tube 56.

Furthermore, since the hollow fibers with their very thin membrane walls provide minimum resistance, permitting the fast flow of gas along the T-piece 42 to pass freely through them, the effect of this configuration on the response time of the analyzer or monitor is negligible even when a large bundle of fibers is used in the element 18. It should also be mentioned that this type of configuration has the advantage that the hydrophobic filter element 18 prevents the sample tube from becoming blocked or filled with patient's excretions, commonly found in the airways, which is often the case with devices of other configurations, without impairing the response time of the device.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A fluid filtering device for separating liquid from gases to be analyzed, comprising:

a tubular housing defining a space therein and having inlet and outlet end portions delimiting passageways in fluid communication with said space, said portions being configured to be connectable between a source of fluid and a gas analyzer, a liquid/gas hydrophobic hollow fiber filter element located within said tubular housing for preventing material other than gases to pass therethrough, and means for effecting substantially smooth and undisturbed fluid flow between said inlet and outlet, said tubular housing and filter element forming a small volume within said housing, and said device being effectively operable independent of its orientation, or field of gravitation acting thereon.

2. The device as claimed in claim 1, wherein at least one of said end portions is provided with a transition section in which the internal fluid flow path leading from said space in the housing to said passageway is gradually restricted and wherein one end portion of said filter element reaches a space delimited by said transition section.

3. The device as claimed in claim 1, wherein said tubular housing and end portions are cylindrical and the cross-sectional area of at least one of said passageways is similar to the cross-sectional area of said space unoccupied by the cross-sectional area of said filter element disposed therein.

4. The device as claimed in claim 2, wherein one end portion of said filter element protrudes into the space delimited by said transition section.

5. The device as claimed in claim 1, further comprising means for trapping filtered out liquid.

6. The device as claimed in claim 5, wherein said means for trapping filtered out liquid is constituted by at least a portion of said tubular housing provided with liquid vapour permeable material.

7. The device as claimed in claim 5, wherein said means for trapping filtered out liquid comprises at least one opening in a wall of said tubular housing.

8. The device as claimed in claim 5, further comprising an outer jacket enclosing at least a portion of said housing and defining liquid collecting space between the outer walls of said housing and the inner wall of said jacket.

9. The device as claimed in claim 8, wherein said liquid collecting space comprises liquid absorbing material.

10. The device as claimed in claim 8, wherein said jacket is provided with means connectable to a vacuum pump for applying a suction action to said collecting space.

11. The device as claimed in claim 10, further comprising a hydrophobic filter for preventing liquid from reaching said vacuum pump.

12. The device as claimed in claim 1, wherein the hollow fibers of said filter element are folded over to form a closed end portion disposed adjacent said inlet portion.

13. The device as claimed in claim 12, further comprising flow blocking means for preventing unfiltered fluid from reaching said outlet end portion.

14. The device as claimed in claim 12, wherein for a flow rate lower than 50 ml/min said tubular housing has a diameter of less than 2.5 mm.

15. The device as claimed in claim 12, wherein for a flow rate of substantially 150 ml/min said tubular housing has a diameter of less than 3.5 mm.

16. The fluid filtering device as claimed in claim 1, wherein said tubular housing is substantially T-shaped and has three openings, a first opening leading to a patient's mouth, a second opposite opening leading to a ventilation system and a third opening leading to a gas analyzer, and said filter element is affixed in the opening leading to a gas analyzer.

17. The fluid filtering device as claimed in claim 16, wherein said hollow fibers have first and a second end portions, said first end portion being affixed in the opening leading to a gas analyzer and said second end portion traverses a line connecting said first and second openings to the extent that it will allow substantially undisturbed ventilation to a patient.

18. The fluid filtering device as claimed in claim 16, wherein said filter element is mounted in a unit having a first portion configured for insertion into said third opening and a nozzle portion, in fluid communication with said first portion to which there is connectable a tube leading to a gas analyzer.

19. The fluid filter device as claimed in claim 18, wherein said unit is disengageable for replacement.

20. A fluid filtering device for separating liquid from gases, comprising:

a tubular housing defining a space therein and having an inlet and an outlet in fluid communication with said space;

a liquid/gas hydrophobic hollow fiber filter element located within said tubular housing and having a wall interposed in a flow path of a liquid-containing fluid, flowing from said inlet to said outlet through said filter element wall, for blocking liquid from reaching said outlet; and flow means for effecting substantially smooth and undisturbed fluid flow between said inlet and said outlet.

21. The device of claim 20, wherein said flow means comprises a first transition section between said inlet and said space, said first transition section defining a passageway in which the fluid flow path is gradually enlarged relative to said inlet.

22. The device of claim 21, wherein said flow means comprises a second transition section between said space and said outlet, said second transition section defining a passageway in which the fluid flow path is gradually restricted relative to said space.

23. The device of claim 22, wherein said flow means comprises locating means for positioning an upstream end of said filter element at said first transition section.

24. The device of claim 23, wherein the upstream end of said filter element is formed as a closed end by the hollow fibers of said filter element being folded over.

25. The device of claim 23, wherein said locating means positions a downstream end of said filter element at said second transition section.

26. The device of claim 25, wherein said flow means comprises said inlet, tubular housing and filter element being so dimensioned that cross sectional areas of said fluid flow path in said inlet and outlet are substantially equal to each other and also to a cross sectional area of the space defined in said housing which is unoccupied by said filter element.

27. The device of claim 25, wherein the filter element comprises a plurality of hollow fibers, and said locating means positions tips of the hollow fibers at the downstream end of said filter element progressively further upstream from said outlet in relation to a transverse distance of such tips from the center of said fluid flow path.

28. The device of claim 20, wherein said flow means comprises a second transition section between said space and said outlet, said second transition section defining a passageway in which the fluid flow path is gradually restricted relative to said space.

29. The device of claim 28, wherein said flow means comprises means for locating a downstream end of said filter element at said second transition section.

30. The device of claim 21, wherein said flow means comprises means for locating an upstream end of said filter element at said first transition section.

31. The device of claim 30, wherein the upstream end of said filter element is formed as a closed end by the hollow fibers of said filter element being folded over.

32. The device of claim 29, wherein the filter element comprises a plurality of hollow fibers, and said locating means positions tips of the hollow fibers at the downstream end of said filter element progressively further upstream from said outlet in relation to a transverse distance of such tips from the center of said fluid flow path.

33. The device of claim 20, wherein said flow means comprises said inlet, tubular housing and filter element being so dimensioned that cross sectional areas of said fluid flow path in said inlet and outlet are substantially equal to each other and also to a cross sectional area of the space defined in said housing which is unoccupied by said filter element.

* * * * *